US009591585B2

(12) United States Patent
Wang et al.

(10) Patent No.: US 9,591,585 B2
(45) Date of Patent: Mar. 7, 2017

(54) TRANSMITTING ANTENNA LEVEL SENSOR OF MAGNETIC RESONANCE IMAGING SYSTEM AND MAGNETIC RESONANCE IMAGING SYSTEM

(71) Applicants: Lan Wang, Shenzhen (CN); Qui Yi Zhang, Shenzhen (CN)

(72) Inventors: Lan Wang, Shenzhen (CN); Qui Yi Zhang, Shenzhen (CN)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/670,682

(22) Filed: Mar. 27, 2015

(65) Prior Publication Data

US 2015/0282095 A1 Oct. 1, 2015

(30) Foreign Application Priority Data

Mar. 28, 2014 (CN) .......................... 2014 1 0123867

(51) Int. Cl.
| | |
|---|---|
| *H01Q 11/12* | (2006.01) |
| *H04W 52/16* | (2009.01) |
| *A61B 5/00* | (2006.01) |
| *H04B 1/04* | (2006.01) |
| *G01R 33/28* | (2006.01) |
| *G01R 33/36* | (2006.01) |
| *A61B 5/055* | (2006.01) |
| *H04W 52/52* | (2009.01) |
| *H04B 17/318* | (2015.01) |

(52) U.S. Cl.
CPC .............. *H04W 52/16* (2013.01); *A61B 5/746* (2013.01); *G01R 33/288* (2013.01); *G01R 33/36* (2013.01); *H04B 1/0483* (2013.01); *A61B 5/055* (2013.01); *H04B 17/318* (2015.01); *H04W 52/52* (2013.01)

(58) Field of Classification Search
CPC ..... H04W 52/16; H04B 1/0483; A61B 5/746; G01R 33/288
USPC .................. 455/522, 91, 114.3, 115.4, 127.1
See application file for complete search history.

(56) References Cited

U.S. PATENT DOCUMENTS

| | | | |
|---|---|---|---|
| 8,723,531 B2* | 5/2014 | Harrison | ................ G01R 27/06 324/637 |
| 2004/0183651 A1* | 9/2004 | Mafune | ................ B60R 25/246 340/5.7 |
| 2010/0036236 A1* | 2/2010 | Fisher | .................... G06F 1/163 600/411 |
| 2011/0095827 A1* | 4/2011 | Tanaka | .................. H03F 1/0261 330/279 |

(Continued)

FOREIGN PATENT DOCUMENTS

| | | |
|---|---|---|
| CN | 1823684 A | 8/2006 |
| DE | 102005007895 A1 | 8/2006 |

*Primary Examiner* — Tuan Pham
(74) *Attorney, Agent, or Firm* — Lempia Summerfield Katz LLC

(57) ABSTRACT

A transmitting antenna level sensor of a magnetic resonance imaging system and a magnetic resonance imaging system is provided. A first detection channel is used for detecting a first power of a first radio frequency signal source, and a second detection channel is used for detecting a second power of the first radio frequency signal source. A control unit is used for comparing the first power with the second power to obtain a first comparison result, and a first notification message is sent according to the first comparison result.

14 Claims, 4 Drawing Sheets

(56) References Cited

U.S. PATENT DOCUMENTS

2013/0114435 A1\* 5/2013 Wang .................... H04W 48/16
370/252

\* cited by examiner

TRANSMITTING ANTENNA LEVEL SENSOR OF MAGNETIC RESONANCE IMAGING SYSTEM AND MAGNETIC RESONANCE IMAGING SYSTEM

This application claims the benefit of CN 201410123867.6, filed on Mar. 28, 2014, which is hereby incorporated by reference in its entirety.

TECHNICAL FIELD

The present embodiments relate to the technical field of magnetic resonance imaging and, more specifically, to a transmitting antenna level sensor of a magnetic resonance imaging system and a magnetic resonance imaging system.

BACKGROUND ART

Magnetic resonance imaging (MRI) is a bio-magnetic nuclear spin imaging technology developed rapidly along with the development of computer technology, electronic circuit technology, and superconductor technology. MRI utilizes a magnetic field and a radio frequency pulse to cause the moving hydrogen nuclei (i.e., H+) within the human tissue to vibrate so as to generate radio frequency signals that are processed by a computer to form an image. When an object is placed in the magnetic field, appropriate electromagnetic waves are irradiated thereon to make the object resonate. Electromagnetic waves released therefrom are then analyzed. Thus, the locations and types of the atomic nuclei that constitute this object may be learned, and based on this, an accurate stereoscopic image of the interior of the object may be drawn. For example, an animation with consecutive slices from the top of the head down to the feet may be obtained by scanning the human brain using magnetic resonance imaging.

In an MRI system, a transmitting antenna level sensor (TALES) is an accurate radio frequency signal voltmeter for measuring a forward and a backward power of a transmitting coil. For example, in CN1823684A, a magnetic resonance tomography imaging system and a high frequency control system are disclosed. The high frequency control system adopts a TALES to measure a forward power that is sent to a high frequency antenna by a sending device and a backward power that is returned by the high frequency antenna.

The TALES is prone to various failures such as ageing after long term usage, thus causing the measurement value to drift from the actual value. In the prior art, in order to overcome various defects caused by the drift error, the TALES is regularly returned to the factory for inspection. However, such a processing method significantly increases various types of costs, and may not find failures promptly when drifts occur.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a transmitting antenna level sensor of a magnetic resonance imaging system that shows the state of the device promptly is provided.

As another example, a magnetic resonance imaging system that finds failures promptly is provided.

A transmitting antenna level sensor of a magnetic resonance imaging system includes a first detection channel for detecting a first power of a first radio frequency signal source, and a second detection channel for detecting a second power of the first radio frequency signal source. The transmitting antenna level sensor also includes a control unit for comparing the first power with the second power to obtain a first comparison result, and for sending a first notification message according to the first comparison result.

The first detection channel includes a first forward detection sub-channel for detecting a first forward power of the first radio frequency signal as the first power. The second detection channel includes a second forward detection sub-channel for detecting a second forward power of the second radio frequency signal as the second power.

The first detection channel contains a first backward detection sub-channel for detecting a first backward power of the first radio frequency signal as the first power. The second detection channel contains a second backward detection sub-channel for detecting a second backward power of the second radio frequency signal as the second power.

The detection structures of the first detection channel and the second detection channel are different.

The first comparison result is that the difference between the first power and the second power is greater than or equal to a predetermined threshold, and the first notification message is an alarm notification.

An alarm unit is further included for receiving the alarm notification and sending an alarm signal.

The first comparison result is that the difference between the first power and the second power is less than a predetermined threshold, and the first notification message is first radio frequency signal source power detection data.

The first radio frequency signal source power detection data is a maximum value, a minimum value, or an average value of the first power and the second power.

Further included are a third detection channel for detecting a third power of a second radio frequency signal source, and a fourth detection channel for detecting a fourth power of the second radio frequency signal source. Further included is the control unit for comparing the third power with the fourth power to obtain a second comparison result, and for sending a second notification message according to the second comparison result.

A magnetic resonance imaging system includes the transmitting antenna level sensor according to any one of the above.

The transmitting antenna level sensor of the magnetic resonance imaging system of one or more of the present embodiments includes a first detection channel for detecting a first power of a first radio frequency signal source, and a second detection channel for detecting a second power of the first radio frequency signal source. The transmitting antenna level sensor also includes a control unit for comparing the first power with the second power to obtain a first comparison result and for sending a first notification message according to the first comparison result. After the embodiments are applied, based on the analysis of respective detection results of collocated detection channels in the transmitting antenna level sensor, various condition information about the types of condition of the transmitting antenna level sensor may be shown promptly, including a failure notification and a detection value notification of the transmitting antenna level sensor.

In addition, the detection sub-channels between various detection channels may have different detection structures, so as to avoid the situation where defects and failures caused by detection structures occur simultaneously in the detection sub-channels, and thus, the reliability of the transmitting antenna level sensor is further improved.

DETAILED DESCRIPTION

Embodiments described herein are merely used for illustrating the present invention and are not intended to limit the scope of protection of the present invention.

A number of details in the embodiments are merely used for helping understand the present invention. The present invention, however, is not limited to these details during implementation. In order to avoid unnecessarily obscuring the present invention, some embodiments are not described in detail, but rather, only frameworks are provided. Hereinafter, the expression "comprising" refers to "comprising, but not limited to," and "according to" refers to "at least according to," but not limited to only according to." When the number of a component is not particularly pointed out, the component may be one and may also be a plurality, or may be understood to be at least one.

Figure 1:
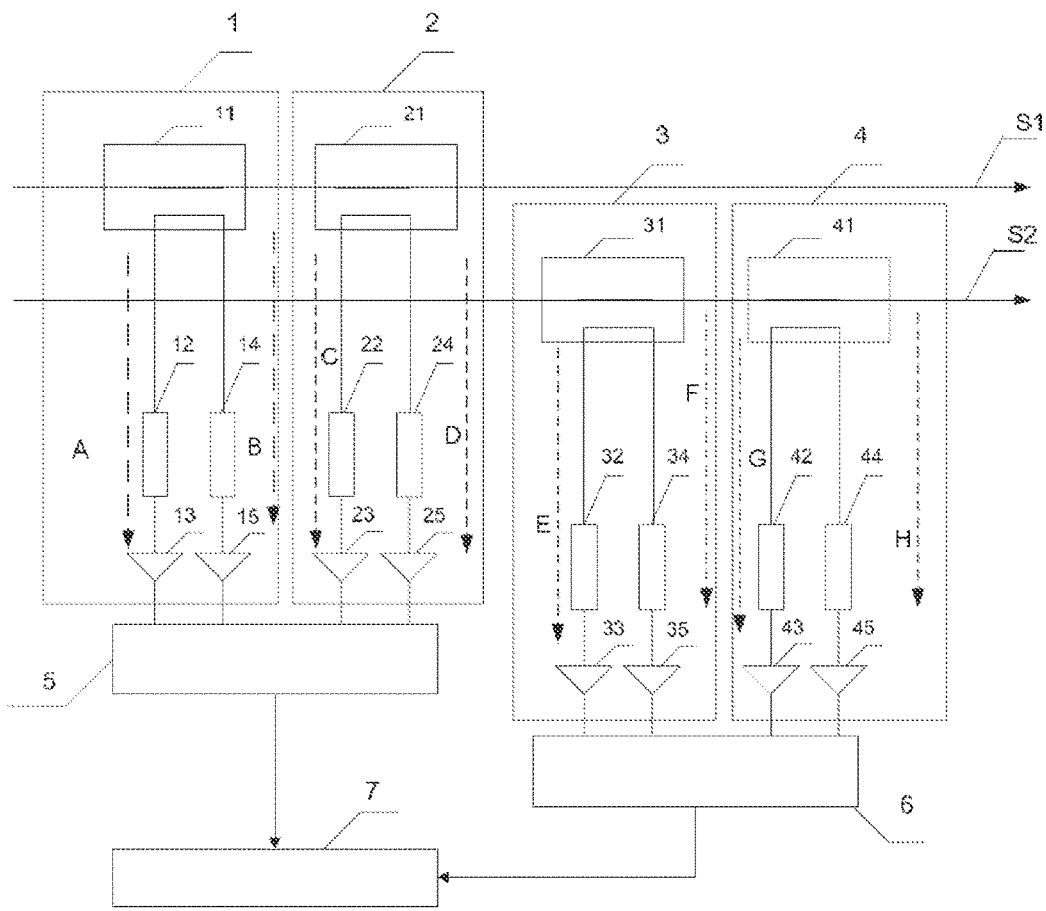
FIG. 1 is a structure diagram of a transmitting antenna level sensor of a magnetic resonance imaging system according to an embodiment.

FIG. 1 is a structure diagram of one embodiment of a transmitting antenna level sensor of a magnetic resonance imaging system.

As shown in FIG. 1, the transmitting antenna level sensor includes a first detection channel 1 for detecting a first power of a first radio frequency signal source S1, and a second detection channel 2 for detecting a second power of the first radio frequency signal source S1. The transmitting antenna level sensor also includes a control unit 7 for comparing the first power with the second power to obtain a first comparison result, and for sending a first notification message according to the first comparison result.

In one embodiment, the first notification message is a first alarm notification message, and the control unit 7 is used for sending the first alarm notification message when the difference between the first power and the second power is greater than a predetermined threshold.

In one embodiment, the first notification message is a first detection value notification message, and the control unit 7 is used for calculating a first average value of the first power and the second power and for generating a first detection value notification message based on the first average value when the difference between the first power and the second power is less than a predetermined threshold.

In one embodiment, an A/D sampling unit 5 is also provided between the first detection channel 1, the second detection channel 2, and the control unit 7.

The A/D sampling unit 5 converts an analog signal value detected by the first detection channel 1 and an analog signal value detected by the second detection channel 2 respectively into digital signal values, and sends the two digital signal values respectively to the control unit 7.

Exemplarily, the control unit 7 may periodically judge whether the two digital signal values are consistent according to a preset time interval and may be triggered when the difference between the two digital signal values exceeds a predetermined threshold. After the control unit 7 is triggered, a prompt may be sent to a user in various ways. For example, the control unit 7 may send an alarm command to a peripheral alarm unit, and after receiving the alarm command, the peripheral alarm unit specifically provides alarms in various forms such as sound, light, etc., so as to prompt the user that a failure has occurred in the transmitting antenna level sensor.

In one embodiment, the transmitting antenna level sensor further includes a third detection channel 3 for detecting a third power of a second radio frequency signal source S2. The transmitting antenna level sensor also includes a fourth detection channel 4 for detecting a fourth power of the second radio frequency signal source S2, and the control unit 7 for sending a second notification message according to the third power and the fourth power.

In one embodiment, the second notification message is a second alarm notification message, and the control unit 7 is used for sending the second alarm notification message when the difference between the third power and the fourth power is greater than a predetermined threshold.

In one embodiment, the second notification message is a second detection value notification message, and the control unit 7 is used for calculating a second average value of the third power and the fourth power and for generating a second detection value notification message based on the second average value when the difference between the third power and the fourth power is less than a predetermined threshold.

In one embodiment, the first radio frequency signal source S1 and the second radio frequency signal source S2 are respectively connected to different output ports of a power divider. For example, the first radio frequency signal source S1 and the second radio frequency signal source S2 have the same power value, and have different phase values. The first radio frequency signal source S1 and the second radio frequency signal source S2 may be respectively connected to different transmitting ports of a transmitting antenna.

In one embodiment, an A/D sampling unit 6 is also provided between the third detection channel 3, the fourth detection channel 4, and the control unit 7.

The A/D sampling unit 6 is used for converting an analog signal value detected by the third detection channel 3 and an analog signal value detected by the fourth detection channel 4 into digital signal values, and for sending the two digital signal values respectively to the control unit 7.

Exemplarily, the control unit 7 may periodically judge whether the two digital signal values are consistent according to a preset time interval and may be triggered when the difference between the two digital signal values exceeds a predetermined threshold. When the control unit 7 is triggered, a prompt may be sent to a user in various ways. For example, the control unit 7 may send an alarm command to a peripheral alarm unit, and after receiving the alarm command, the peripheral alarm unit specifically provides alarms in various forms such as sound, light, etc., so as to prompt the user that a failure has occurred in the transmitting antenna level sensor.

In one embodiment, when judging that the difference between the detection value of the first detection channel 1 and the detection value of the second detection channel 2 has exceeded a predetermined threshold, the control unit 7 sends a prompt according to a predetermined method, such as controlling an alarm diode to emit red light. In addition, when judging that the difference between the detection value of the third detection channel 3 and the detection value of the fourth detection channel 4 has exceeded a predetermined threshold, the control unit 7 sends a prompt according to another predetermined method, such as controlling an alarm diode to emit blue light. Thus, the user may locate an approximate region of the failure based on the color emitted by the alarm diode, and facilitate subsequent corresponding processing such as maintenance, replacement, etc.

In one embodiment, the first detection channel 1 contains a first directional coupler 11 for coupling a first radio frequency signal from the first radio frequency signal source S1. The first detection channel 1 also contains a first forward detection sub-channel A for detecting a first forward power of the first radio frequency signal. The first forward detection sub-channel A specifically includes a radio frequency attenuator 12 and a power detector 13. The input of the radio frequency attenuator 12 is connected to an output end of the first directional coupler 11. The input of the power detector 13 is connected to the output of the radio frequency attenuator 12. The output of the power detector 13 is connected to the A/D sampling unit 5. The first detection channel 1 includes a first backward detection sub-channel B for detecting a first backward power of the first radio frequency signal. The first backward detection sub-channel B specifically includes a radio frequency attenuator 14 and a power detector 15. The input of the radio frequency attenuator 14 is connected to another output end of the first directional coupler 11. The input of the power detector 15 is connected to the output of the radio frequency attenuator 14, and the output of the power detector 15 is connected to the A/D sampling unit 5.

In addition, the second detection channel 2 contains a second directional coupler 21 that is collocated with the first directional coupler 11 and is used for coupling a second radio frequency signal from the first radio frequency signal source S1. The second detection channel 2 contains a second forward detection sub-channel C for detecting a second forward power of the second radio frequency signal. The second forward detection sub-channel C includes a radio frequency attenuator 22 and a power detector 23. The input of the radio frequency attenuator 22 is connected to an output end of the first directional coupler 21. The input of the power detector 23 is connected to the output of the radio frequency attenuator 22, and the output of the power detector 23 is connected to the A/D sampling unit 5. The second detection channel 2 contains a second backward detection sub-channel D for detecting a second backward power of the second radio frequency signal. The second backward detection sub-channel D includes a radio frequency attenuator 24 and a power detector 25. The input of the radio frequency attenuator 24 is connected to another output end of the first directional coupler 21. The input of the power detector 25 is connected to the output of the radio frequency attenuator 24, and the output of the power detector 25 is connected to the A/D sampling unit 5. The second detection channel 2 also contains the control unit 7 for sending a first notification message according to the first forward power and the second forward power, and/or for sending the first notification message according to the first backward power and the second backward power.

Exemplarily, the first notification message is a first alarm notification message.

The control unit 7 is used for sending the first alarm notification message when the difference between a detection value (e.g., the first forward power) of the first forward detection sub-channel A and a detection value (e.g., the second forward power) of the second forward detection sub-channel C exceeds a predetermined threshold, and/or for sending the first alarm notification message when the difference between a detection value (e.g., the first backward power) of the first backward detection sub-channel B and a detection value (e.g., the second backward power) of the second backward detection sub-channel D exceeds a predetermined threshold.

The control unit 7 may judge whether a failure has occurred in the forward power detection of the first radio frequency signal source S1 through the respective forward detection sub-channels (e.g., the first forward detection sub-channel A and the second forward detection sub-channel C) in two collocated detection channels (e.g., the first detection channel 1 and the second detection channel 2). In addition, the control unit 7 may judge whether a failure has occurred in the backward power detection of the first radio frequency signal source S1 through the respective backward detection sub-channels (e.g., the first backward detection sub-channel B and the second backward detection sub-channel D) in two collocated detection channels (e.g., the first detection channel 1 and the second detection channel 2).

Exemplarily, the first notification message is a first detection value notification message.

In one embodiment, the control unit 7 is used for calculating a forward power average value of the first forward power and the second forward power and for generating a first detection value notification message based on the forward power average value when the difference between the first forward power and the second forward power is less than a predetermined threshold. Additionally or alternatively, the control unit 7 is used for calculating a backward power average value of the first backward power and the second backward power and for generating the first detection value notification message based on the backward power average value when the difference between the first backward power and the second backward power is less than a predetermined threshold.

In one embodiment, the control unit 7 is used for calculating a maximum value of the first forward power and the second forward power and for generating a first detection value notification message based on the maximum value when the difference between the first forward power and the second forward power is less than a predetermined threshold. Additionally or alternatively, the control unit 7 is used for calculating a maximum value of the first backward power and the second backward power and for generating the first detection value notification message based on the maximum value when the difference between the first backward power and the second backward power is less than a predetermined threshold.

In one embodiment, the control unit 7 is used for calculating a minimum value of the first forward power and the second forward power and for generating a first detection value notification message based on the minimum value when the difference between the first forward power and the second forward power is less than a predetermined threshold. Alternatively or additionally, the control unit 7 is used for calculating a minimum value of the first backward power and the second backward power and for generating the first detection value notification message based on the minimum value when the difference between the first backward power and the second backward power is less than a predetermined threshold.

In one embodiment, the third detection channel 3 contains a third directional coupler 31 for coupling a third radio frequency signal from the second radio frequency signal source S2. The third detection channel 3 also contains a third forward detection sub-channel E for detecting a third forward power of the third radio frequency signal. The third forward detection sub-channel E includes a radio frequency attenuator 32 and a power detector 33. The input of the radio frequency attenuator 32 is connected to an output end of the third directional coupler 31. The input of the power detector 33 is connected to the output of the radio frequency attenuator 32. The output of the power detector 33 is connected to the A/D sampling unit 6. The third detection channel 3 contains a third backward detection sub-channel F for detecting a third backward power of the third radio frequency signal. The third backward detection sub-channel F includes a radio frequency attenuator 34 and a power detector 35. The input of the radio frequency attenuator 34 is connected to another output end of the third directional coupler 31. The input of the power detector 35 is connected to the output of the radio frequency attenuator 34. The output of the power detector 35 is connected to the A/D sampling unit 6.

In addition, the fourth detection channel 4 contains a fourth directional coupler 41 that is collocated with the second directional coupler 11 and is used for coupling a fourth radio frequency signal from the second radio frequency signal source S2. The fourth detection channel 4 also contains a fourth forward detection sub-channel G for detecting a fourth forward power of the fourth radio frequency signal. The fourth forward detection sub-channel G includes a radio frequency attenuator 42 and a power detector 43. The input of the radio frequency attenuator 42 is connected to an output end of the fourth directional coupler 41. The input of the power detector 43 is connected to the output of the radio frequency attenuator 42. The output of the power detector 43 is connected to the A/D sampling unit 6. The fourth detection channel 4 also contains a fourth backward detection sub-channel H for detecting a fourth backward power of the fourth radio frequency signal. The fourth forward detection sub-channel H includes a radio frequency attenuator 44 and a power detector 45. The input of the radio frequency attenuator 44 is connected to another output end of the fourth directional coupler 41. The input of the power detector 45 is connected to the output of the radio frequency attenuator 44, and the output of the power detector 45 is connected to the A/D sampling unit 5. The fourth detection channel 4 includes the control unit 7 for sending a second notification message according to the third forward power and fourth forward power, and/or for sending the second notification message according to the third backward power and the fourth backward power.

Exemplarily, the second notification message is a second alarm notification message.

The control unit 7 is used for sending the second alarm notification message when the difference between a detection value (e.g., the third forward power) of the third forward detection sub-channel E and a detection value (e.g., the fourth forward power) of the fourth forward detection sub-channel G exceeds a predetermined threshold. Alternatively or additionally, the control unit 7 is used for sending the second alarm notification message when the difference between a detection value (e.g., the third backward power) of the third backward detection sub-channel F and a detection value (e.g., the fourth backward power) of the fourth backward detection sub-channel H exceeds a predetermined threshold.

The control unit 7 may judge whether a failure has occurred in the forward power detection of the second radio frequency signal source S2 through the respective forward detection sub-channels (e.g., the third forward detection sub-channel E and the fourth forward detection sub-channel G) in two collocated detection channels (e.g., the third detection channel 3 and the fourth detection channel 4). In addition, the control unit 7 may judge whether a failure has occurred in the backward power detection of the second radio frequency signal source S2 through the respective backward detection sub-channels (e.g., the third backward detection sub-channel F and the fourth backward detection sub-channel H) in two collocated detection channels (e.g., the third detection channel 3 and the fourth detection channel 4).

Exemplarily, the second notification message is a second detection value notification message.

In one embodiment, the control unit 7 is used for calculating a forward power average value of the third forward power and the fourth forward power and for generating the second detection value notification message based on the forward power average value when the difference between the third forward power and the fourth forward power is less than a predetermined threshold. Alternatively or additionally, the control unit 7 is used for calculating a backward power average value of the third backward power and the fourth backward power and for generating the second detection value notification message based on the backward power average value when the difference between the third backward power and the fourth backward power is less than a predetermined threshold.

In one embodiment, the control unit 7 is used for calculating a maximum value of the third forward power and the fourth forward power and for generating the second detection value notification message based on the maximum value when the difference between the third forward power and the fourth forward power is less than a predetermined threshold. Alternatively or additionally, the control unit 7 is used for calculating a maximum value of the third backward power and the fourth backward power and for generating the second detection value notification message based on the maximum value when the difference between the third backward power and the fourth backward power is less than a predetermined threshold.

In one embodiment, the control unit 7 is used for calculating a minimum value of the third forward power and the fourth forward power and for generating the second detection value notification message based on the minimum value when the difference between the third forward power and the fourth forward power is less than a predetermined threshold. Alternatively or additionally, the control unit 7 is used for calculating a minimum value of the third backward power and the fourth backward power and for generating the second detection value notification message based on the minimum value when the difference between the third backward power and the fourth backward power is less than a predetermined threshold.

In one embodiment, the first forward detection sub-channel A and the second forward detection sub-channel C have different detection structures. In this way, the situation where defects and failures caused by detection structures occur simultaneously in the first forward detection sub-channel A and the second forward detection sub-channel C may be avoided. Similarly, the first backward detection sub-channel B and the second backward detection sub-channel D have different detection structures. In this way, the situation where defects and failures caused by detection structures occur simultaneously in the first backward detection sub-channel B and the second backward detection sub-channel D may be avoided.

In one embodiment, the third forward detection sub-channel E and the fourth forward detection sub-channel G have different detection structures. In this way, the situation where defects and failures caused by detection structures occur simultaneously in the third forward detection sub-channel E and the fourth forward detection sub-channel G may be avoided. Similarly, the third backward detection sub-channel F and the fourth backward detection sub-channel H have different detection structures. In this way, the situation where defects and failures caused by detection structures occur simultaneously in the third backward detection sub-channel F and the fourth backward detection sub-channel H may be avoided.

In the above-mentioned description, the control unit 7 may determine whether to give an alarm for the power detection of the first radio frequency signal source S1 based on the difference between the detection value of the first detection channel 1 and the detection value of the second detection channel 2. Other detection channels for detecting the power of the first radio frequency signal source S1 may also be provided, and at this moment, the control unit 7 may determine, based on a plurality of judgment criteria such as pairwise judgment, overall judgment, etc., and according to the detection results of various detection channels that are detected with regard to the power of the first radio frequency signal source S1, whether to trigger the alarm.

Similarly, other detection channels for detecting the power of the second radio frequency signal source S2 may also be provided, and at this moment, the control unit 7 may determine, based on a plurality of judgment criteria such as pairwise judgment, overall judgment, etc., and according to the detection results of various detection channels that are detected with regard to the power of the second radio frequency signal source S2, whether to trigger the alarm.

Figure 2:
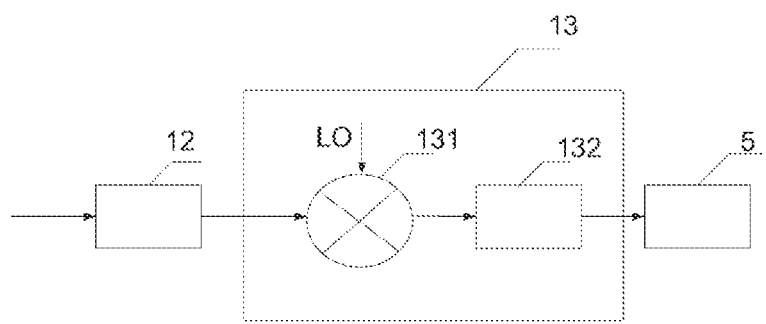
FIG. 2 is a structure diagram of a first forward detection sub-channel in a first detection channel according to an embodiment.
Figure 3:
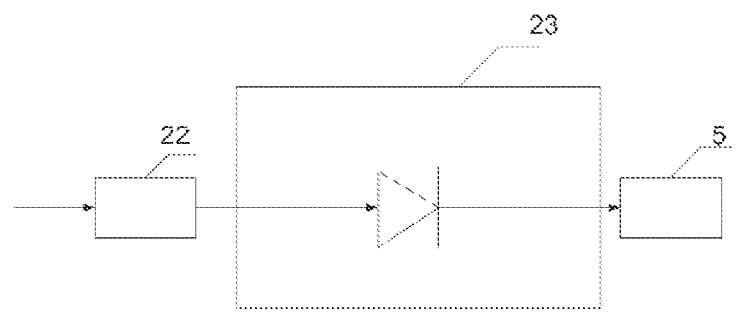
FIG. 3 is a structure diagram of a second forward detection sub-channel in a second detection channel according to an embodiment.

FIG. 2 is a structure diagram of a first forward detection sub-channel A in a first detection channel according to an embodiment. FIG. 3 is a structure diagram of a second forward detection sub-channel C in a second detection channel according to an embodiment.

FIG. 2 shows that the radio frequency attenuator 12 attenuates the radio frequency signals provided by the radio frequency signal source and sends the radio frequency signals to the power detector 13. The power detector 13 includes a mixer 131 and a low-pass filter 132. The mixer 131 mixes the radio frequency signal and a local oscillator signal (LO) together and sends the mixed signal to the low-pass filter 132. The low-pass filter 132 obtains a radio frequency signal power value through filtering and sends the radio frequency signal power value to the A/D sampling unit 5. The A/D sampling unit 5 converts the radio frequency signal power value into a digital signal and sends the radio frequency signal power value to the control unit 7.

FIG. 3 shows that the radio frequency attenuator 22 attenuates the radio frequency signals provided by the radio frequency signal source and sends the radio frequency signals to the power detector 23. The power detector 23 may be implemented as a logarithmic amplifier or a diode detector. The logarithmic amplifier or the diode detector calculates a radio frequency signal power value and sends the radio frequency signal power value to the A/D sampling unit 5. The A/D sampling unit 5 converts the radio frequency signal power value into a digital signal and sends the radio frequency signal power value to the control unit 7.

The first forward detection sub-channel A in the first detection channel and the second forward detection sub-channel C in the second detection channel respectively adopt different power detection structures.

Alternatively, the first backward detection sub-channel B in the first detection channel and the second backward detection sub-channel D in the second detection channel also respectively adopt different power detection structures.

The third forward detection sub-channel E in the third detection channel may also adopt a structure similar to that of the first forward detection sub-channel A in the first detection channel. The fourth forward detection sub-channel G in the fourth detection channel may also adopt a structure similar to that of the second forward detection sub-channel C in the second detection channel.

Exemplarily, the first forward detection sub-channel A, the first backward detection sub-channel B, the third forward detection sub-channel E, and the third backward detection sub-channel F respectively adopt the structure as shown in FIG. 2. The second forward detection sub-channel C, the second backward detection sub-channel D, the fourth forward detection sub-channel G, and the fourth backward detection sub-channel H respectively adopt the structure as shown in FIG. 3.

Figure 4:
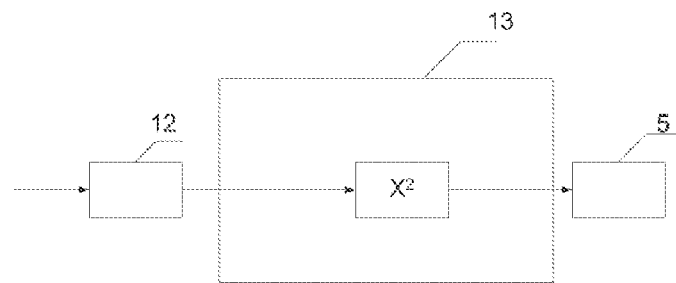
FIG. 4 is a structure diagram of the first forward detection sub-channel in the first detection channel according to another embodiment.
Figure 5:
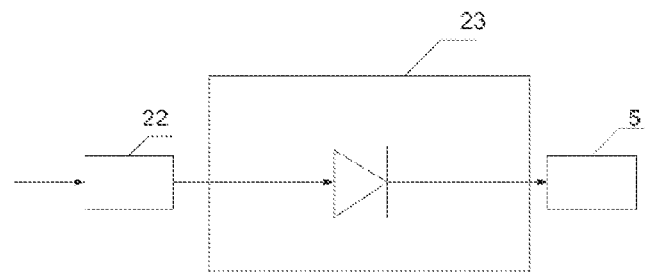
FIG. 5 is a structure diagram of the second forward detection sub-channel in the second detection channel according to another embodiment.

FIG. 4 is a structure diagram of the first forward detection sub-channel A in the first detection channel according to another embodiment. FIG. 5 is a structure diagram of the second forward detection sub-channel C in the second detection channel according to another embodiment.

FIG. 4 shows that the radio frequency attenuator 12 attenuates the radio frequency signals provided by the radio frequency signal source and sends the radio frequency signals to the power detector 13. The power detector 13 may be implemented as an RMS detector. The RMS detector calculates a radio frequency signal power value and sends the calculated radio frequency signal power value to the A/D sampling unit 5. The A/D sampling unit 5 converts the radio frequency signal power value into a digital signal and sends the radio frequency signal power value to the control unit 7.

FIG. 5 shows an example where the radio frequency attenuator 22 attenuates the radio frequency signals provided by the radio frequency signal source and sends the radio frequency signals to the power detector 23. The power detector 23 may, for example, be implemented as a logarithmic amplifier or a diode detector. The logarithmic amplifier or the diode detector calculates a radio frequency signal power value, and then sends the calculated radio frequency signal power value to the A/D sampling unit 5. The A/D sampling unit 5 converts the radio frequency signal power value into a digital signal and sends the radio frequency signal power value to the control unit 7.

Exemplarily, the first forward detection sub-channel A, the first backward detection sub-channel B, the third forward detection sub-channel E, and the third backward detection sub-channel F respectively adopt the structure as shown in FIG. 4, and the second forward detection sub-channel C, the second backward detection sub-channel D, the fourth forward detection sub-channel G, and the fourth backward detection sub-channel H respectively adopt the structure as shown in FIG. 5.

The specific structures of the detection sub-channels are described above in detail, and those skilled in the art will appreciate that such description is merely exemplary, and is not intended to limit the scope of protection of the embodiments of the present invention.

The power of a transmitting antenna of a magnetic resonance imaging system may be detected based on the transmitting antenna level sensor provided in one or more of the present embodiments.

Figure 6:
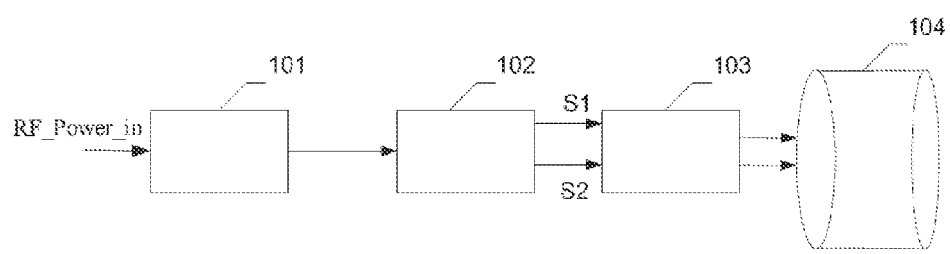
FIG. 6 is a schematic diagram of transmitting antenna power detection of a magnetic resonance imaging system according to an embodiment.

FIG. 6 is a schematic diagram of transmitting antenna power detection of a magnetic resonance imaging system according to one or more of the present embodiments.

As shown in FIG. 6, the transmitting antenna is specifically implemented as a body coil 104.

The input end (RF_Power_in) of a radio-frequency power amplifier 101 is connected to a radio frequency signal input source, whereas the output end of the radio-frequency power amplifier 101 is connected to a 90-degree power divider 102. The 90-degree power divider 102 divides the radio frequency signals input by the radio-frequency power amplifier 101 into two paths. The two paths of radio frequency signals respectively correspond to the first radio frequency signal source S1 and the second radio frequency signal source S2. In addition, the powers of the two paths of radio frequency signals are the same, and the phases thereof are respectively 0 degree and 90 degrees. A transmitting antenna level sensor 103 may respectively detect the powers of the first radio frequency signal source S1 and the second radio frequency signal source S2. The body coil 104 respectively transmits the two paths of radio frequency signals via different transmitting ports.

Hereinabove, the body coil is taken as an example to describe one or more of the present embodiments. Those skilled in the art will appreciate that such description is merely exemplary, and is not intended to limit the scope of protection of the embodiments of the present invention. The embodiments are applicable to any radio frequency coils in a magnetic resonance imaging system in the field of health care, including but not limited to body coils, neck coils, head coils, and the like.

Hereinabove, the magnetic resonance imaging system in the field of health care is taken as an example to describe one or more of the present embodiments in detail. Those skilled in the art will appreciate that such description is merely exemplary, and is not intended to limit the scope of protection of the embodiments of the present invention. One or more of the present embodiments are applicable to other fields and, more specifically, also to magnetic resonance imaging systems used in research or industrial fields.

Based on the above-mentioned detailed analysis, one or more of the present embodiments also provide a power detection method for a transmitting antenna of a magnetic resonance imaging system.

Figure 7:
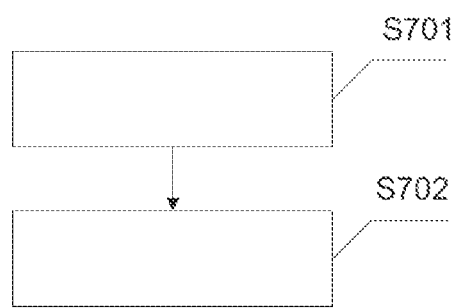
FIG. 7 is a flowchart of a power detection method for a transmitting antenna of a magnetic resonance imaging system according to an embodiment.

FIG. 7 is a flowchart of a power detection method for a transmitting antenna of a magnetic resonance imaging system according to one or more of the present embodiments.

As shown in FIG. 7, the method includes the following acts: act S701, a first detection channel is enabled to detect a first power of a first radio frequency signal source, and a second detection channel is enabled to detect a second power of the first radio frequency signal source; and act S702, the first power is compared with the second power to obtain a first comparison result, and a first notification message is sent according to the first comparison result.

In one embodiment, the method also includes: a third detection channel that is enabled to detect a third power of a second radio frequency signal source, and a fourth detection channel that is enabled to detect a fourth power of the second radio frequency signal source; and the third power is compared with the fourth power to obtain a second comparison result, and a second notification message is sent according to the second comparison result. The first radio frequency signal source and the second radio frequency signal source respectively acquire radio frequency signals from different output ports of a power divider.

Not all of the acts and modules in each of the above-mentioned flows and structural schematic diagrams are necessary, and it is possible to ignore certain acts or modules according to actual needs. The execution sequence of each act is not fixed and may be adjusted as needed. The division of various modules is merely a division in functions adopted for the purpose of facilitating description, and in actual implementation, one module may be respectively implemented by a plurality of modules. The functions of the plurality of modules may also be implemented by the same module, and these modules may be located in the same device and may also be located in different devices.

Hardware modules in each embodiment may be implemented mechanically or electrically. For example, a hardware module may include a specially designed permanent circuit or logic device (e.g., a dedicated processor, such as FPGA or ASIC) for completing a specific operation. The hardware module may also include a programmable logic device or circuit (e.g., including a general-purpose processor or other programmable processors) that is configured by software temporarily for carrying out a specific operation. It may be determined, according to the considerations of cost and time, whether to implement the hardware module specifically adopting the mechanical manner, adopting a dedicated permanent circuit, or adopting a circuit that is temporarily configured (e.g., configured by software).

One or more of the present embodiments also provide a machine readable storage medium that stores instructions for making a machine carry out the method as described herein. A system or a device with a storage medium may be provided. Software program codes for implementing the functions of any of the above-mentioned embodiments are stored on the storage medium, and a computer (e.g., either CPU or MPU) of the system or device is enabled to read and execute the program codes stored in the storage medium. In addition, an operating system running in a computer may be enabled to complete part of or all of the actual operations by instructions based on the program codes. The program codes read from the storage medium may also be written into a memory provided in an extension board inserted inside the computer or into a memory provided in an extension unit connected to the computer. Subsequently, the instructions based on the program codes cause the CPU mounted on the extension board or the extension unit to carry out part of or all of the practical operations, thereby realizing the function of any one of the above-mentioned embodiments.

The embodiments of the storage medium for providing program codes include a floppy disk, a hard disk, a magnetic optical disk, an optical disk (e.g., CD-ROM, CD-R, CD-RW, DVD-ROM, DVD-RAM, DVD-RW, and DVD+RW), a magnetic tape, a non-volatility memory card, and a ROM. Selectively, the program codes may be downloaded from a server computer via a communication network.

In summary, the transmitting antenna level sensor of the magnetic resonance imaging system of one or more of the present embodiments include: a first detection channel for detecting a first power of a first radio frequency signal source; a second detection channel for detecting a second power of the first radio frequency signal source; and a control unit for comparing the first power with the second power to obtain a first comparison result, and sending a first notification message according to the first comparison result. After the embodiments are applied, based on the analysis of respective detection results of the collocated detection channels in the transmitting antenna level sensor, various types of information about the condition of the transmitting antenna level sensor may be shown promptly, including a failure notification and a detection value notification of the transmitting antenna level sensor.

In addition, the detection sub-channels between various detection channels may have different detection structures, so as to avoid the situation where defects and failures caused by detection structures occur simultaneously in the detection sub-channels. Thus, the reliability of the transmitting antenna level sensor is further improved.

The above description provides embodiments of the present invention, but is not intended to limit the scope of protection of the present invention. Any amendments, equivalent substitutions, improvements, etc. within the spirit and principle of the present invention should all be included in the scope of the protection of the present invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A transmitting antenna level sensor of a magnetic resonance imaging system, the transmitting antenna level sensor comprising:
    a first detection channel for detecting a first power of a first radio frequency signal source at one position;
    a second detection channel for detecting a second power of the first radio frequency signal source at the same one position;
    a third detection channel for detecting a third power of a second radio frequency signal source;
    a fourth detection channel for detecting a fourth power of the second radio frequency signal source; and
    a control unit configured to:
        compare the first power with the second power to obtain a first comparison result;
        send a first notification message according to the first comparison result;
        compare the third power with the fourth power to obtain a second comparison result; and
        send a second notification message according to the second comparison result,
    wherein detection structures of the first detection channel and the second detection channel are different.

2. The transmitting antenna level sensor of claim 1, wherein the first detection channel comprises a first forward detection sub-channel for detecting a first forward power of the first radio frequency signal as the first power, and
    wherein the second detection channel comprises a second forward detection sub-channel for detecting a second forward power of the second radio frequency signal as the second power.

3. The transmitting antenna level sensor of claim 1, wherein the first detection channel contains a first backward detection sub-channel for detecting a first backward power of the first radio frequency signal as the first power, and
    wherein the second detection channel contains a second backward detection sub-channel for detecting a second backward power of the second radio frequency signal as the second power.

4. The transmitting antenna level sensor of claim 1, wherein the first comparison result is that a difference between the first power and the second power is greater than or equal to a predetermined threshold, and
    wherein the first notification message is an alarm notification.

5. The transmitting antenna level sensor of claim 4, further comprising an alarm unit operable to receive the alarm notification and send an alarm signal.

6. The transmitting antenna level sensor of claim 2, wherein the first comparison result is that a difference between the first power and the second power is less than a predetermined threshold, and
    wherein the first notification message is first radio frequency signal source power detection data.

7. The transmitting antenna level sensor of claim 6, wherein the first radio frequency signal source power detection data is a maximum value, a minimum value or an average value of the first power and the second power.

8. A magnetic resonance imaging system comprising:
    a transmitting antenna level sensor comprising:
        a first detection channel for detecting a first power of a first radio frequency signal source at one position;
        a second detection channel for detecting a second power of the first radio frequency signal source at the same one position;
        a third detection channel for detecting a third power of a second radio frequency signal source;
        a fourth detection channel for detecting a fourth power of the second radio frequency signal source; and
        a control unit configured to:
            compare the first power with the second power to obtain a first comparison result;
            send a first notification message according to the first comparison result;
            compare the third power with the fourth power to obtain a second comparison result; and
            send a second notification message according to the second comparison result,
        wherein detection structures of the first detection channel and the second detection channel are different.

9. The magnetic resonance imaging system of claim 8, wherein the first detection channel comprises a first forward detection sub-channel for detecting a first forward power of the first radio frequency signal as the first power, and
    wherein the second detection channel comprises a second forward detection sub-channel for detecting a second forward power of the second radio frequency signal as the second power.

10. The magnetic resonance imaging system of claim 8, wherein the first detection channel contains a first backward detection sub-channel for detecting a first backward power of the first radio frequency signal as the first power, and wherein the second detection channel contains a second backward detection sub-channel for detecting a second backward power of the second radio frequency signal as the second power.

11. The magnetic resonance imaging system of claim 8, wherein the first comparison result is that a difference between the first power and the second power is greater than or equal to a predetermined threshold, and
wherein the first notification message is an alarm notification.

12. The magnetic resonance imaging system of claim 11, wherein the transmitting antenna level sensor further comprises an alarm unit operable to receive the alarm notification and send an alarm signal.

13. The magnetic resonance imaging system of claim 9, wherein the first comparison result is that a difference between the first power and the second power is less than a predetermined threshold, and
wherein the first notification message is first radio frequency signal source power detection data.

14. The magnetic resonance imaging system of claim 13, wherein the first radio frequency signal source power detection data is a maximum value, a minimum value or an average value of the first power and the second power.

* * * * *